(12) United States Patent
Cacas et al.

(10) Patent No.: US 9,730,442 B2
(45) Date of Patent: Aug. 15, 2017

(54) USE OF 4-PHENYLBUTYRIC ACID FOR IMPROVING THE TOLERANCE OF PLANTS TO HARMFUL BIOLOGICAL ORGANISMS

(71) Applicant: INSTITUT DE RECHERCHE POUR LE DÉVELOPPEMENT (IRD), Marseille (FR)

(72) Inventors: Jean-Luc Cacas, La Tour D'aigues (FR); Antony Champion, Quissac (FR)

(73) Assignee: INSTITUT DE RECHERCHE POUR LE DÉVELOPPEMENT (IRD), Marseilles (FR)

( * ) Notice: Subject to any disclaimer, the term of this patent is extended or adjusted under 35 U.S.C. 154(b) by 0 days.

(21) Appl. No.: 14/414,062

(22) PCT Filed: Jul. 10, 2013

(86) PCT No.: PCT/EP2013/064547
§ 371 (c)(1),
(2) Date: Jan. 9, 2015

(87) PCT Pub. No.: WO2014/009402
PCT Pub. Date: Jan. 16, 2014

(65) Prior Publication Data
US 2015/0201618 A1    Jul. 23, 2015

(30) Foreign Application Priority Data
Jul. 11, 2012 (FR) ...................... 12 56660

(51) Int. Cl.
*A01N 37/10*    (2006.01)
(52) U.S. Cl.
CPC ................... *A01N 37/10* (2013.01)
(58) Field of Classification Search
CPC ...................................... A01N 37/10
USPC ........................................ 514/570
See application file for complete search history.

(56) References Cited

U.S. PATENT DOCUMENTS

| | | |
|---|---|---|
| 6,245,717 B1 | 6/2001 | Dean et al. |
| 6,372,938 B1 | 4/2002 | Burzynski et al. |
| 2010/0261694 A1 | 10/2010 | Lam et al. |
| 2011/0124554 A1 | 5/2011 | Godson et al. |
| 2012/0077677 A1 | 3/2012 | Willms et al. |

FOREIGN PATENT DOCUMENTS

WO    WO-2014/009402 A1    1/2014

OTHER PUBLICATIONS

Lee et al., Mol. Cells, (2012), vol. 34, pp. 109-116.*
Steinmann et al., Antimicrob. Agents Chemotherap. (2009), vol. 53(12), pp. 5127-5133.*
Cohen et al., Therapeutic approaches to protein-misfolding diseases, Nature, 426(6968): 905-909 (2003).
Maestri et al., Long-term treatment of girls with ornithine transcarbamylase deficiency, N. Engl. J. Med., 335(12): 855-859 (1996).
International Searching Authority, Written Opinion for PCT/EP2013/064547, mailed Aug. 5, 2013.
International Searching Authority, International Search Report for PCT/EP2013/064547, mailed Aug. 5, 2013.

* cited by examiner

*Primary Examiner* — Taofiq A Solola
(74) *Attorney, Agent, or Firm* — Marshall, Gerstein & Borun LLP

(57) ABSTRACT

The present invention relates to the use of 4-phenylbutyric acid, or one of the salts thereof, for improving the resistance of plants to harmful biological organisms, in particular to bacteria, viruses and nematodes, and for inhibiting hypersensitive cell death induced by such harmful biological organisms. The present invention also relates to the use of 4-phenylbutyric acid, or one of the salts thereof, as an antimicrobial agent for preventing or treating plant diseases caused by phytopathogens.

5 Claims, 5 Drawing Sheets

A

B

USE OF 4-PHENYLBUTYRIC ACID FOR IMPROVING THE TOLERANCE OF PLANTS TO HARMFUL BIOLOGICAL ORGANISMS

RELATED APPLICATIONS

The present application is filed pursuant to 35 U.S.C. §371 as a U.S. National Phase Application of international application No. PCT/EP2013/064547, which was filed on Jul. 10, 2013, claiming the benefit of priority of French application No. FR 1 256 660 filed on Jul. 11, 2012. The entire content of each of the aforementioned applications is incorporated herein by way of reference in its entirety.

FIELD OF THE INVENTION

The present invention relates to the use of 4-phenylbutyric acid for improving plant resistance to harmful biological organisms, in particular to bacteria, to viruses and to nematodes.

CONTEXT OF THE INVENTION

Combating plant diseases is a major preoccupation in agriculture. It is estimated that, worldwide, approximately a third of harvests are destroyed in the field or during storage by pathogenic agents (insects, viruses, bacteria, oomycetes or fungi). This is reflected by considerable economic losses and can, in certain regions of the world, result in problems of under-nourishment or of malnutrition of populations.

Over the course of time, several approaches have been developed for combating plant diseases, the oldest being the chemical approach which calls upon pesticides, such as fungicides, bactericides, nematocides, virucides and insecticides. Although effective, the use of molecules derived from the chemical industry is generally associated with problems of pollution and with potential risks to human and animal health. Furthermore, numerous phytopathogens of viral or bacterial origin are not sensitive to the chemical products currently available on the market, and certain pathogenic fungi, acarids, nematodes and insects can withstand high doses of pesticides without damage.

Alternatives to chemical treatments have since been developed and are commonly used in the field or are gradually reaching the market. Mention should in particular be made of biological control which uses organisms that are natural predators against plant pathogenic agents; genetic improvement of plants, which remains one of the methods of choice when stable resistance or tolerance genes, which can be introduced into the hereditary material of plants, have been identified; and methods based on the natural resistance of plants to diseases caused by pests.

The natural resistance of plants to diseases caused by pests is often initiated by the specific recognition of a given pathogen, and particularly by the recognition of molecules called "elicitors" or "effectors" present at the surface of pathogens or excreted by said pathogens. This recognition results in a rapid induction of the defence mechanisms of the plant, which limit the multiplication and the propagation of the pathogen in the various plant tissues. Studies have shown that the application of the elicitors to a plant increases the resistance of said plant to harmful biological organisms by preventively activating its defence reactions. This stimulation of the natural defences has opened the way to new approaches in terms of combating plant diseases and is increasingly arousing interest. However, the elicitors have the disadvantage of having a limited spectrum of action and of still being too expensive.

The majority of the already existing methods based on the exploitation of the natural defence mechanisms of the plants are based on the activation of hypersensitive cell death in contexts where the plant does not normally do this. Although these methods undoubtedly lead to resistance, they result in the death of the infected tissues. Even though this death is to the benefit of the rest of the plant, a loss of yield results therefrom.

Despite the progress made, there is thus still a need for novel strategies for combating plant diseases caused by pathogenic agents.

SUMMARY OF THE INVENTION

Generally, the present invention is based on the use of 4-phenylbutyric acid (4-PBA) in the field of agriculture. The inventors have in fact shown that 4-PBA inhibits hypersensitive cell death induced by phytopathogenic agents and that the application of 4-PBA to plants makes it possible to improve their resistance to these agents without affecting the yield of the plants. The inventors have also demonstrated that, in addition to its effects on plants, 4-PBA exhibits antimicrobial properties toward phytopathogenic agents. Compared with the chemical active ingredients currently available on the market, 4-PBA has the advantage of not being toxic to humans or to the environment at the doses used, including to the plants to which it is administered. Furthermore, it is relatively inexpensive.

Consequently, in a first aspect, the present invention relates to the use of 4-PBA, or one of the salts thereof, for improving the resistance of a plant to a phytopathogen chosen from bacteria, viruses and nematodes.

In certain embodiments, this use is characterized in that the 4-PBA, or one of the salts thereof, prevents a plant disease caused by the phytopathogen.

In certain embodiments, this use is characterized in that the 4-PBA, or one of the salts thereof, inhibits hypersensitive cell death induced, in the plant, by the phytopathogen.

The invention thus also relates to the use of 4-PBA, or one of the salts thereof, for inhibiting cell death induced, in a plant, by a phytopathogen chosen from bacteria, viruses and nematodes.

In another aspect, the invention relates to the use of 4-PBA, or one of the salts thereof, as an antimicrobial agent for preventing or treating a disease caused, in a plant, by a phytopathogen.

In certain embodiments, the phytopathogen is chosen from bacteria, viruses and nematodes.

Preferably, in the uses according to the invention, the phytopathogen is biotrophic.

The invention also provides methods for implementing the invention.

Thus, the invention relates to a method for improving the resistance of a plant to a phytopathogen chosen form bacteria, viruses and nematodes, the method comprising the application of 4-PBA, or one of the salts thereof, to the plant or to the soil surrounding the plant.

In certain embodiments, the method is characterized in that the 4-PBA, or one of the salts thereof, inhibits hypersensitive cell death induced by the phytopathogen.

The invention also relates to a method for preventing or treating a plant disease caused by a phytopathogen, comprising the application, to the plant or to the soil surrounding the plant, of a sufficient amount of 4-PBA, or one of the salts thereof, in order to destroy the phytopathogen and/or to inhibit the growth of the phytopathogen.

In certain embodiments, the method is characterized in that the phytopathogen is chosen from bacteria, viruses and nematodes. The phytopathogen is preferably biotrophic.

In certain embodiments, the uses and the methods according to the invention are characterized in that the 4-PBA, or one of the salts thereof, is applied pre-emergence of the plant.

Alternatively or additionally, the 4-PBA, or one of the salts thereof, can be applied post-emergence of the plant.

In certain embodiments, the 4-PBA, or one of the salts thereof, is applied to the aerial parts of the plant, to the roots of the plant, to the seeds, tubers or bulbs of the plant, and/or to the fruits or grains of the plant.

In certain embodiments, the uses and the methods according to the invention are characterized in that the plant belongs to the family Malvaceae, to the family Solanaceae, to the family Rubiaceae, to the family Poaceae or Gramineae or to the family Vitaceae.

A more detailed description of certain preferred embodiments of the invention is given below.

DETAILED DESCRIPTION OF THE INVENTION

Figure 1:
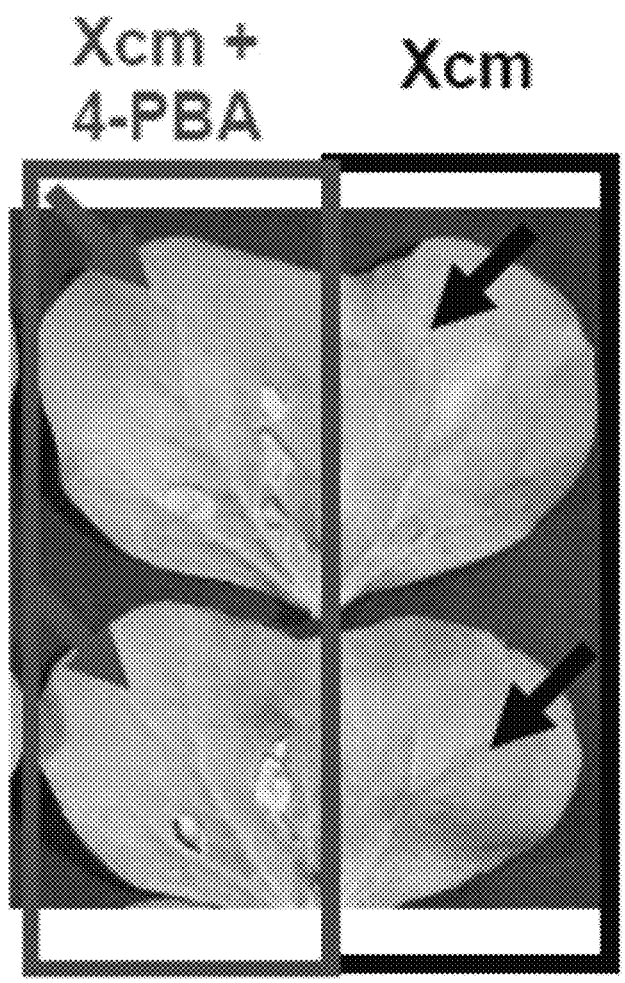
FIG. 1 shows that 4-PBA strongly repressed the hypersensitive symptoms normally induced by the infiltration of the Xcm bacterium into cotton plant cotyledonary leaves.

As mentioned above, the present invention relates to the use of 4-phenylbutyric acid (4-PBA) for improving the resistance of plants to harmful biological organisms without affecting their yield. In particular, the 4-PBA can be used for improving the resistance of plants to bacteria, to viruses and to nematodes; for inhibiting hypersensitive cell death induced by these phytopathogens; and/or for destroying these phytopathogens and/or limiting the growth and reproduction thereof.

I—4-Phenylbutyric Acid and the Salts Thereof

4-Phenylbutyric acid (also known as 4-phenylbutanoic acid) is a small molecule which, owing to its biological properties, has found use in the pharmaceutical field and the use of which in the field of agriculture has recently been proposed.

4-PBA is a chaperone molecule, i.e. a molecule which assists proteins in their maturation by providing them with appropriate three-dimensional folding (Cohen et al., Nature, 2003, 426: 905-909). Several studies have shown that, in mammals, 4-PBA inhibits endoplasmic reticulum stress and abolishes the triggering of the UPR (Upfolded Protein Response). 4-PBA is approved for the treatment of urea cycle diseases (Maestri et al., N. Engl. J. Med., 1996, 335: 855-859), and has been proposed as a therapeutic agent in the treatment of pathological conditions such as type 2 diabetes and neurodegenerative diseases.

In plants, it has been reported that the application of 4-PBA to crops makes it possible to control the production of auxin (a plant growth phytohormone) and thus to increase the yields of said crops (U.S. Pat. No. 6,245,717). The application of 4-PBA to plants has also been described as resulting in an improvement in the resistance of plants to abiotic stresses, such as drought, heat or aridity (application US 2012/0077677). Finally, it has been demonstrated that it is possible to prevent *Fusarium* ear blight, a disease which affects crops and which is caused by a necrotrophic fungus of the *Fusarium* genus, by application of chaperone molecules, such as 4-PBA, to crops (application US 2010/0261694).

In the context of the invention, the 4-PBA can be used in the form of 4-phenylbutyric acid or in the form of one of the salts thereof. The term "4-PBA salt" is intended to mean any compound obtained by reacting 4-PBA, acting as an acid, with an appropriate base so as to form, for example, a salt of an alkali metal, such as sodium, potassium and lithium; a salt of an alkaline-earth metal, such as calcium and magnesium; a salt of a transition metal, such as manganese, copper, zinc and iron; an ammonium salt; a phosphonium salt; a sulfonium salt; an oxonium salt; a choline salt; or else a salt with an organic base containing a nitrogen atom, such as trimethylamine, triethylamine, tributylamine, N,N-dimethylaniline, N-methylpiperidine, N-methylmorpholine, diethylamine, dicyclohexylamine, dibenzylamine, pyridine, guanidine, hydrazine and quinine. Preferably, a 4-PBA salt used in the implementation of the present invention is a sodium, potassium, calcium, magnesium, manganese, copper, zinc, iron, ammonium, phosphonium, sulfonium, or oxonium salt.

The 4-PBA can be synthesized by any method, for example by reacting benzene with butyrolactone in the presence of aluminum chloride, followed by neutralization in the presence of a base, as described in U.S. Pat. No. 6,372,938.

Generally, the 4-PBA, or one of the salts thereof, is applied to the plants in the form of an aqueous solution. It can be used alone or in combination with other substances, such as, for example, insecticides, acaricides, fungicides, nematicides, bactericides, herbicides, phytoprotectors, growth regulators, nutritive elements supplements, and/or fertilizers.

II—Use of 4-phenylbutyric Acid for Improving the Resistance of Plants to Phytopathogens The present inventors have shown that 4-PBA improves the resistance of plants to phytopathogenic agents. Contrary to the natural resistance of plants, which is based on the activation of hypersensitive cell death and results in the death of the infected tissues, the resistance resulting from the application of 4-PBA occurs without affecting the yield of the plants. Indeed, the inventors have shown that 4-PBA inhibits hypersensitive cell death induced by phytopathogens, and thus avoids the death of the infected tissues.

The term "resistance to phytopathogens" is intended to denote herein a series of advantages for plants. Such advantages can manifest themselves, for example, through a decrease in the predisposition of a plant to develop a disease caused by a phytopathogen; an improvement in the ability of a plant to combat a disease caused by a phytopathogen; a decrease in the presence, in the plant, of the number and/or of the seriousness of the symptoms of a disease caused by a phytopathogen; an improvement in the storage stability of the plant once harvested (and/or of its fruits once picked); an improvement in the appearance of the plant due to the absence or to the presence of a limited number of sites of necrosis, of burns, of spots, of rot, of galls, of tumors or of withering in the tissues of the plant; an improvement in biomass; an improvement in root growth; an improvement in the stolon production; an increase in leaf surface area; an improvement in sexual and/or vegetative reproduction; an increase in the number of flowers; an increase in fruit volume; an improvement in fruit appearance; an increase in the concentration of nutritive elements and of constituents such as, for example, carbohydrates, lipids, proteins, vitamins, minerals and fibers; a decrease in the amount of toxic or unfavorable products contained in the plant, etc.

In the aforementioned, an improvement, an increase or a decrease in a property is generally by at least 3%, preferably by at least 5%, and even more preferably by at least 10% relative to a plant which has not been treated with 4-PBA, or one of the salts thereof.

The invention therefore relates to the use of 4-PBA, or one of the salts thereof, for improving the resistance of plants to phytopathogenic agents.

The invention also relates to the use of 4-PBA, or one of the salts thereof, for preventing a plant disease caused by a phytopathogenic agent.

The invention also relates to the use of 4-PBA, or one of the salts thereof, for inhibiting hypersensitive cell death induced, in a plant, by a phytopathogenic agent. As used herein, the term "hypersensitive cell death" denotes the death of the plant tissues infected with a pathogen, which results from the hypersensitive response (HR), a defense reaction by the plant which is set up in response to an invasion by a pathogenic agent.

Pathogenic Agents

The term "phytopathogenic agents" or "phytopathogens", is intended to denote herein microorganisms capable of infecting plants and of triggering diseases therein. In the context of the present invention, the phytopathogenic agent is preferably a bacterium, a virus or a nematode. The invention relates more particularly to the improvement of the resistance of plants to biotrophic phytopathogenic agents, i.e. microorganisms which feed themselves to the detriment of the plant.

In particular, the 4-PBA can be used for improving the resistance of plants to phytopathogenic bacteria. Such phytopathogenic bacteria can belong to the group of α-proteobacteria, which contain the bacteria of the *Bacterium* genus (which, on contact with a wound, can cause, in virtually all dicotyledons, galls or sometimes root proliferation) and the bacteria of the *Rhizobium* genus (which live in symbiosis with the roots of leguminous plants); or to the group of β-proteobacteria, which contain the bacteria of the *Burkholderia* genus (which cause withering, rot or necroses) and the bacteria of the *Ralstonia solanacerum* genus (which are responsible for vascular diseases in tropical regions); or else to the group of γ-proteobacteria, which contain the bacteria of the *Erwinia* genus (which are responsible for significant plant diseases).

The 4-PBA can in particular be used for improving the resistance of plants to bacteria of the *Xanthomonas* genus, in particular the species *X. campestris, X. albilineans, X alfalfae, X. ampelina, X. arboricola, X. axonopodis, X. boreopolis, X. badnii, X. bromi, X. cassavae, X. citri, X. codiaei, X. cucurbitae, X. cyanopsidis, X. cynarae, X. euvesicatoria, X. fragariae, X. hortorum, X. hyacinthi, X. malvacearum, X. manihotis, X. melonis, X. oryzae, X. papavericola, X. perforans, X. phaseoli, X. pisi, X. populi, X. sacchari, X. theicola, X. translucens, X. vasicola* and *X. vesicatoria.*

The bacteria of the species *Xanthomonas campestris* can in particular belong to the pathovars *armoraciae, begoniae A, begoniae B, campestris, carotae, corylina, dieffenbachiae, hederae, hyacinthi, juglandis, malvacearum, musacearum, nigromaculans, pelargonii, phaseoli, poinsettiicola, raphani, sesami, tardicrescens, translucens* and *vesicatoria*, which attack numerous plant species of agronomic interest, such as rice, cabbage, bean, fruits of citrus type such as lemon, sugar cane, etc.

The 4-PBA can also be used for improving the resistance of plants to bacteria of the *Pseudomonas* genus, in particular the species *P. syringae, P. amygdali, P. avellanae, P. agarici, P. alcaligenes, P. asplenii, P. aurantiaca, P. aureofaciens, P. balearica, P. brassicacearum, P. cannabina, P. caricapapayae, P. cichorii, P. coronafaciens, P. cedrina, P. chlororaphis, P. corrugata, P. cissicola, P. citronellolis, P. congelans, P. costantinii P. gengiri, P. extremorientalis, P. ficuserectae, P. flavescens, P. flectens, P. fluorescens, P. fuscovaginae, P. gessardii P. grimontii P. jessenii, P. kilonensis, P. lanceolata, P. libanensis, P. helianthi, P. lini, P. lundensis, P. meliae, P. reactans, P. resinovorans, P. rhodesiae, P. savastanoi, P. saccharophila, P. mediterranea, P. marginalis, P. mandelii, P. salomonii, P. putida, P. tolaasii, P. trivialis, P. tremae, P. veronii* and *P. viridiflava.*

The bacteria of the species *Pseudomonas syringae* can in particular belong to the pathovars *aceris, aptata, apii, antirrhini, avii, atrofaciens, atropurpurea, dysoxylis, japonica, lapsa, panici, papulans, pisi, syringae, aesculi, actinidiae, nigromaculans, pelargonii, glycenea, maculicola, passiflorae, persicae, phaseoli, poinsettiicola, raphani, sesami, spinaceae, tabaci, tardicrescens, theae, tomato, translucens* and *vesicatoria*, which attack numerous plants of agronomic interest, including tomato, soya, tobacco, bean, lemon tree, pear tree, pea, cherry tree, etc. The 4-PBA, or one of the salts thereof, can in particular be used for improving the resistance of a plant to the bacterium *Pseudomonas solanacearum*, also called *Ralstonia solanacearum* or *Burkholderia Solanacearum*, which is present on all the continents, particularly in tropical and subtropical regions. This bacterium is in particular the agent of potato brown rot, of Granville tobacco wilt and of Moko disease of banana.

The 4-PBA can also be used for improving the resistance of plants to bacteria of the *Erwinia* genus, in particular the species *E. amylovora* which causes bacterial fire blight in pear trees and apple trees, *E. carotovora* which is pathogenic to numerous fruits and vegetables (carrot, beetroot, turnip, tomato, potato, etc.), *E. aphidicola, E. billingiae, E. chrysanthemi, E. mallotivora, E. papayae, E. persicina, E. psidii, E. pyrifoliae, E. rhapontici, E. tasmaniensis, E. toletana* and *E. tracheiphila*. The 4-PBA, or one of the salts thereof, can in particular be used for improving the resistance of a plant to the bacterium *E. chrysanthemi*, also called *Dickeyq dadantii*, which causes soft rot disease. The 4-PBA, or one of the salts thereof, can also be used in the case of the bacterium *Erwinia carotovora* subsp. *atroseptica*, also called *Pectobacterium atrosepticum*, which causes the symptoms of soft rot and of blackleg in potato.

The 4-PBA can also be used for improving the resistance of plants to bacteria of the *Agrobacterium* genus, in particular the species *A. tumefaciens* which is responsible for a disease called crown gall and which is reflected by the formation of a tumor at the site of infection, and the species *A. vitis* which is responsible for hairy root, a disease characterized by the appearance of a root hair at the point of infection.

The 4-PBA can also be used for improving the resistance of plants to pathogenic viruses of the Bigeminivirus, Monogeminivirus, Hybrigeminivirus, Ipomovirus, Macluravirus, Nanavirus, Ourmiavirus, Satellite RNA, Satellivirus and Varicosavirus family. Examples of such phytoviruses include the phytopathogenic viruses of the *Alfamovirus, Begomovirus, Benyvirus, Caulimovirus, Carlavirus, Comovirus, Crinivirus, Cucumovirus, Curtovirus, Ilarvirus, Nucleorhabodovirus, Nepovirus, Poleroverus, Pomovirus, Potexvirus, Potyvirus, Sobemovirus, Tymovirus, Trichovirus, Tobamovirus, Tobravirus* and *Tospovirus* genera.

Other pathogenic viruses include potato virus A, Andean potato latent virus, beet curly top virus, potato leafroll virus, grapevine leafroll-associated virus, Solanum apical leaf curling virus, potato mop-top virus, potato yellow dwarf virus, tomato spotted wilt virus, Andean potato mottle virus, potato aucuba mosaic virus, alfalfa mosaic virus, wild potato mosaic virus, tomato mosaic virus, cauliflower mosaic virus, Sowbane mosaic virus, cucumber mosaic virus, maize mosaic virus, tobacco mosaic virus, potato yellow mosaic virus, tomato yellow leaf curl virus, potato yellow vein virus, potato yellowing virus, potato virus M, chestnut mosaic virus, potato virus S, potato virus T, potato virus U, potato virus V, potato virus X and potato virus Y.

The 4-PBA can also be used for improving the resistance of plants to pathogenic nematodes. Examples of such nematodes include the phytopathogenic nematodes of the *Aphelenchoides, Achlysiella, Anguina, Aulosphora, Bursaphelenchus, Ditylenchus, Discocriconemella, Globofera, Heterodera, Helicotylenchus, Hirschmanniella, Longidorus, Meloidogyne, Nacobbus, Paratrichodorus, Pratylenchus, Radopholus, Rotylenchulus, Trichodorus, Tylenchorhynchus, Scutellonema* and *Xiphinema* genera.

Thus, the plant diseases that it is possible to prevent according to the invention include any disease caused by a phytopathogenic agent such as those mentioned above.

Plants

The invention can be applied to a wide variety of plants, including large-scale crop plants, edible plants, flowers and trees.

In particular, the invention can be applied to dicotyledonus plants, such as in particular Malvaceae (for example, cotton plant, etc.), Solanaceae (for example, tobacco, tomato, potato, eggplant, etc.), Cucurbitaceae (for example, melon, cucumber, water melon, squash, etc.), cruciferous plants or Brassicaceae (for example, rapeseed, mustard, etc.), composites (for example, chicory, etc.), Umbelliferae (for example, carrot, cumin, etc.), or Rosaceae (in particular trees and shrubs of which the fruits are of economic significance), or monocotyledons, such as, for example, in particular cereals (for example, wheat, barley, oats, rice, corn, etc.) or Liliaceae (for example, onion, garlic, etc.).

In certain preferred embodiments, the 4-PBA is applied to a plant belonging to the family Malvaceae (for example, cotton plant, cocoa, okra, etc.) to the family Solanaceae (for example, tobacco, tomato, potato, eggplants, etc.), to the family Rubiaceae (for example, coffee, etc.), to the family Poaceae or Gramineae (for example, rice, corn, wheat, barley, oats, rye, millet, sugar cane, etc.) or to the family Vitaceae (for example, grapevine, etc.).

In certain embodiments, the 4-PBA is applied to a transgenic plant, the term "transgenic plant" is intended to mean a plant which has been obtained by means of genetic manipulation techniques. More specifically, a transgenic plant is a plant in which at least one cell contains exogenous nucleotide sequences introduced by means of a human intervention. Typically, the transgenic plants express DNA sequences which confer on these plants one or more characteristics other than those of non-transgenic plants of the same species.

III—Use of 4-phenylbutyric Acid as an Antimicrobial Agent

The present inventors have demonstrated an antibacterial effect of 4-PBA on certain phytopathogenic bacteria. The term "antibacterial" is intended to denote herein a substance which kills (bactericidal effect) and/or which slows down (bacteriostatic effect) the growth and/or multiplication of bacteria.

Consequently, the invention relates to the use of 4-PBA, or one of the salts thereof, as an antimicrobial agent for preventing and/or treating plant diseases caused by phytopathogens. As used herein, the term "antimicrobial" refers to a substance which kills and/or inhibits the growth and/or multiplication of microorganisms.

The plant diseases that it is a priori possible to treat according to the invention include any disease caused by a phytopathogenic agent which is destroyed and/or the growth of which is inhibited by 4-PBA or one of the salts thereof.

In particular, the 4-PBA, or one of the salts thereof, can be used for treating a disease caused by a bacterium of the species *Xanthomonas campestris*, belonging in particular to the pathovars *armoraciae, begoniae A, begoniae B, campestris, carotae, corylina, dieffenbachiae, hederae, hyacinthi, juglandis, malvacearum, musacearum, nigromaculans, pelargonii, phaseoli, poinsettiicola, raphani, sesami, tardicrescens, translucens* or *vesicatoria*.

Because of its antimicrobial properties, 4-PBA, or one of the salts thereof, can have an application in numerous fields where the absence of microbial contamination, in particular bacterial and/or viral contamination, is desired. Thus, for example, 4-PBA, or one of the salts thereof, can have an application in the field of maintenance and hygiene products as a disinfecting agent. The term "disinfecting", as used herein, denotes a substance which kills and/or inhibits the growth and/or reproduction of microorganisms on the surface of inanimate objects. Such objects may, for example, be medical instruments; floors, surfaces, furniture or devices of laboratories or of operating sites; floors, surfaces, furniture or devices in private homes or in public or industrial premises.

The invention therefore also includes the use of 4-PBA, or one of the salts thereof, as a disinfecting agent. According to this same aspect, the present invention also comprises a method for cleaning, decontaminating or disinfecting a surface of an object, comprising a step of bringing the surface of the object into contact with an effective amount of 4-PBA, or one of the salts thereof. The 4-PBA, or one of the salts thereof, can be included in a cleaning product or composition, or can impregnate a pad or a wipe intended for cleaning, for decontaminating and/or for disinfecting. The invention encompasses such compositions, products, pads and wipes.

IV—Methods for Using 4-phenylbutyric Acid

Methods or processes are also provided for implementing the invention. In the methods of the invention, the phytopathogenic agents, the plants and the plant diseases are as described above.

Thus, the invention relates to a method for improving the resistance of a plant to a pathogenic agent, characterized in that it comprises the application of 4-PBA, or one of the salts thereof, to the plants and/or to the soils surrounding the plants.

In certain particular embodiments, the 4-PBA, or one of the salts thereof, is applied in an amount which is sufficient (or effective) for inhibiting hypersensitive cell death induced by the phytopathogen.

In other particular embodiments, the 4-PBA, or one of the salts thereof, is applied in an amount which is sufficient (or effective) for preventing a plant disease caused by the phytopathogen.

The invention also relates to a method of destroying a phytopathogen and/or of inhibiting the growth of said phytopathogen for preventing or treating a plant disease caused by the phytopathogen, comprising the application, to the plant or to the soil surrounding the plant, of a sufficient (or effective) amount of 4-PBA acid. The phytopathogen can be chosen from bacteria, viruses and nematodes.

Application of 4-PBA to Plants

In the implementation of the invention, the application of 4-PBA, or one of the salts thereof, can be carried out by any method known in the art. For example, the application can be carried out by treatment of the soil or on the soil (by sprinkling, injection or spraying); by treatment of crop substrates (soil-based compost, compost); by treatment with nutritive solutions or irrigation (dropwise system or by spraying); by treatment of the aerial parts of the plant (by sprinkling or spraying, or by fumigation in the case of greenhouse crops); by treatment of the seeds or of other propagation materials (for example, by dusting of tubers or of plants); by dipping bulbs, fruits, cuttings or plants; by drenching fruits; or by treatment of stored grains.

In the context of the present invention, the term "aerial parts of a plant" is intended to mean the portion of the plant that is commonly referred to as foliage, and which is above the soil. Generally, the aerial part or foliage of a plant comprises the leaves, the stems, the flowers and the fruits. The definition of the term "fruit" herein is that which is used in botany, and said term therefore denotes the plant organ containing one or more seeds. The term "fruit" therefore also encompasses vegetables.

Depending on the phytopathogen/plant pair and on the desired effect (i.e. improvement of the resistance of the plant and/or antimicrobial effect), those skilled in the art know how to determine the most appropriate mode(s) of application.

Those skilled in the art also know how to determine the optimal dose(s) of 4-PBA, or one of the salts thereof, to be applied in order to obtain the desired result. Generally, the dose applied corresponds to a concentration which is nontoxic to humans and to the environment. In certain embodiments, the 4-PBA, or one of the salts thereof, is applied to the plants to be treated, or parts of plants to be treated, by spraying. In these embodiments, the 4-PBA, or one of the salts thereof, is preferably applied in a dose ranging from 0.0005 to 3 kg/ha, more preferably ranging from 0.001 to 2 kg/ha, and even more preferably from 0.005 to 1 kg/ha.

In the context of the present invention, the 4-PBA, or one of the salts thereof, can be applied pre-emergence and/or post-emergence of the plant. The terms "pre-emergence of the plant" and "pre-sprouting of the plant" are used herein without distinction and denote the period after sewing before the cultivated plant emerges from the ground. The terms "post-emergence of the plant" and "post-sprouting of the plant" are used herein without distinction and denote the period in which the plant has emerged from the ground.

Alternatively or additionally, the 4-PBA, or one of the salts thereof, can be applied after harvesting of the plant or of its fruits, in order to improve the storage stability of the plant or of the fruits.

Unless otherwise defined, all the technical and scientific terms used in the description have the same meaning as that commonly understood by an ordinary specialist in the field to which this invention belongs. Likewise, all the publications and patent applications, all the patents and any other references mentioned herein are incorporated by way of reference.

EXAMPLES

The following examples describe certain embodiments of the present invention. However, it is understood that the examples are presented solely by way of illustration only and do not in any way limit the scope of the invention.

Example 1

Inhibitory Effect of 4-PBA on Hypersensitive Cell Death

Figure 2:
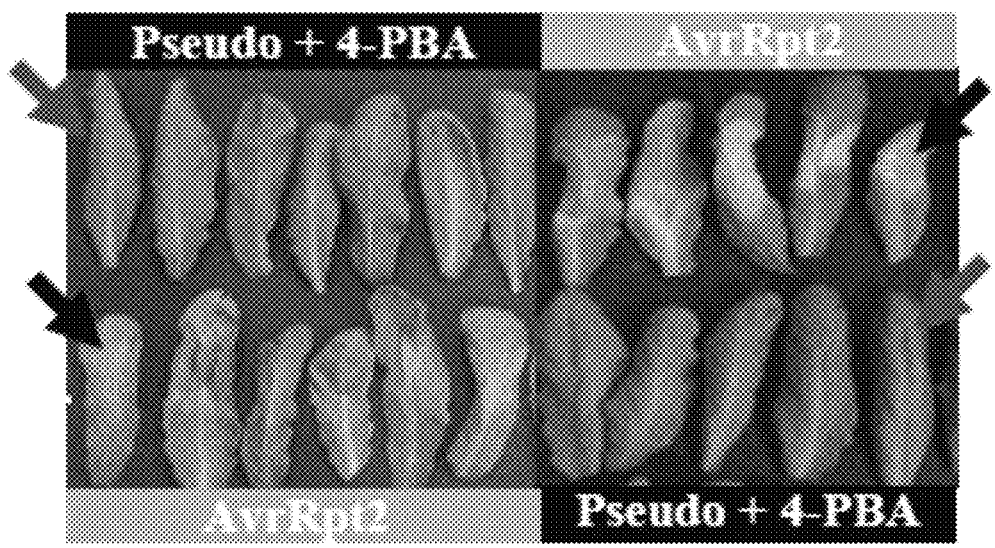
FIG. 2 shows that 4-PBA abolished the hypersensitive symptoms normally induced by the infiltration of the Xcm bacterial into *A. thaliana* leaves.

The effect of 4-PBA on cell death of hypersensitive nature was tested on several pathosystems, including those presented in FIGS. 1 & 2, namely *Gossypium hirsutum/Xanthomonas campestris* pv. *malvacearum* and *Arabidopsis thaliana/Pseudomonas syringae*. pv. *tomato*, respectively. Other data, although not presented, confirm the anti-cell death properties of 4-PBA when the latter is applied to plant tissues. The latter data concern hypersensitive cell death induced in tobacco by an elicitor of fungal origin, cryptogein, and nonhost hypersensitive cell death in tobacco interacting with the bacterium *Pseudomonas syringae* pv. *tomato*.

Materials and Methods

A stock solution of 4-PBA (10 mM) was prepared extemporaneously by dissolving powder in sterile distilled water. In order to allow complete dissolution of the 4-PBA, the solution was heated at 50° C. for 10 minutes.

The *Xanthomonas campestris* pv. *malvacearum* bacteria (Xcm, race 18) were cultured overnight in a rich nutritive medium (King B). After sedimentation by centrifugation, said bacteria were washed with sterile distilled water before being resuspended at a concentration of $10^8$ cfu/ml. The resuspending of the cells is carried out either in sterile distilled water, or in a solution of 4-PBA at 2 mM. These two types of suspensions were infiltrated into cotton plant (*Gossypium hirsutum*) cotyledons on each side of the central vein for comparison. The macroscopic symptoms observed four days after inoculation are presented in FIG. 1. This experiment was repeated twice with comparable results.

The bacteria (Pst, avirulent strain DC3000::AvrRpt2) were cultured overnight in a rich nutritive medium (King B). After sedimentation by centrifugation, said bacteria were washed with sterile distilled water before being resuspended at a concentration of $10^7$ cfu/ml. The resuspending of the cells is carried out either in sterile distilled water, or in a solution of 4-PBA at 1 mM. These suspensions were then infiltrated into the leaves of the *Arabidopsis thaliana* rosette. The macroscopic symptoms were monitored over a period of six days post-inoculation. This experiment was repeated twice with comparable results.

Results

The results regarding the cell death induced by the Xcm bacterium (avirulent strain race 18) on the cotton plant cotyledons are presented in FIG. 1. They clearly show that 4-PBA strongly represses the hypersensitive symptoms (arrows on the left part of FIG. 1) normally induced by the infiltration of the bacterium into cotton plant cotyledonary leaves (arrows on the right part of FIG. 1).

The results regarding the cell death induced by the *Pseudomonas* bacterium on the leaves of *Arabidopsis thaliana* are presented in FIG. 2. They show that 4-PBA is also capable of abolishing the hypersensitive symptoms normally induced by the infiltration of the bacterium into *A. thaliana* leaves.

Example 2

Effects of 4-PBA on Plant Endoplasmic Reticulum

The effect of 4-PBA on the endoplasmic reticulum of plant cells was tested on two types of plants: thale cress (*Arabidopsis thaliana*) and tobacco (*Nicotiana tabacum*).
Materials and Methods The 4-PBA solutions used in the experiments described hereinafter were prepared as described in Example 1.

The infection with Pst (avirulent strain DC3000::AvrRpt2) was carried out under the same conditions as those described above. An additional condition was added, corresponding to the infiltration of a solution of 4-PBA (1 mM) alone into the *A. thaliana* leaves.

Samples were harvested 44 hours post-inoculation, frozen in liquid nitrogen and then stored at −80° C. until total RNA extraction. The total RNA was reverse transcribed so as to synthesize cDNAs. These cDNAs were used as a template in real-time quantitative PCR experiments. Primers specific for the genes encoding the binding proteins (BiP1,2 and BiP3), calnexin 1 (CNX1) and calreticulin 1 (CRT1) were designed so as to measure the expression of these genes. The expression of the genes of interest was standardized with respect to that of an actin gene. These experiments were repeated once, including one as a duplicate per experiment.

Figure 3:
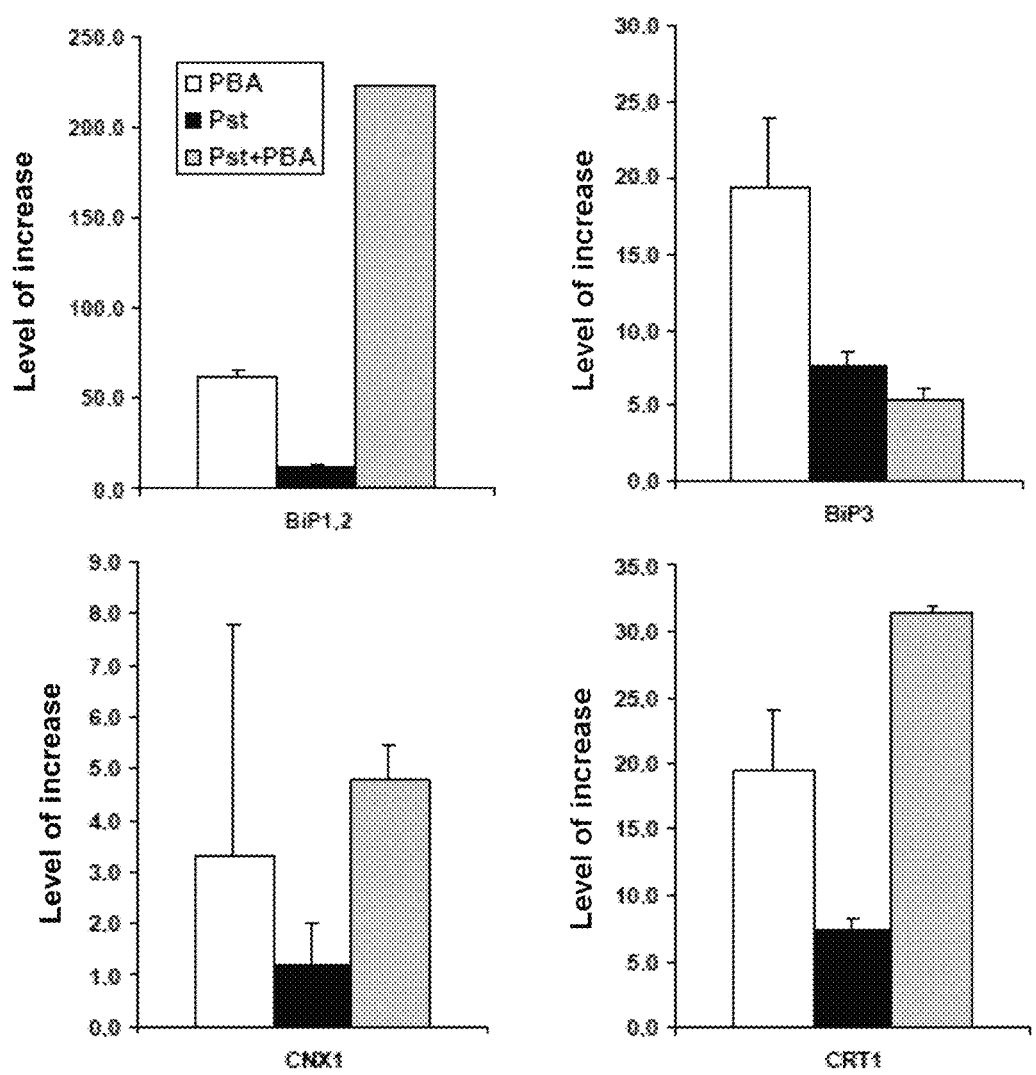
FIG. 3 shows that 4-PBA when infiltrated alone into thale cress leaves, significantly induced the expression of genes encoding chaperone proteins located at the level of the endoplasmic reticulum.

The concentration range presented in FIG. 4A was produced by infiltration into tobacco leaves of 4-PBA solutions at 0.5, 1, 2.5 and 5 mM. The macroscopic symptoms were evaluated 48 hours post-infiltration. Samples were also harvested at the times indicated in FIG. 4B and treated as described above so as to be analyzed by real-time quantitative PCR. Primers specific for all of the nine genes encoding BiP proteins were designed for this purpose.
Results The results obtained for A. thaliana are presented in FIG. 3. They clearly show that 4-PBA, when it is infiltrated alone into thale cress leaves, makes it possible to significantly induce the expression of genes encoding chaperone proteins (i.e. BiP1, 2 and BiP3, CNX1 and CRT1) located at the level of the endoplasmic reticulum. Furthermore, the infiltration of the Pst bacterium alone induces a lower expression of four of the genes under consideration, suggesting a stress of the reticulum in response to the infection. Finally, a synergistic effect of 4-PBA and of the infection with the bacterium can be observed for the BiP1,2, CNX1 and CRT1 genes. All of these data strongly suggest that 4-PBA abolishes hypersensitive cell death induced by Pst by increasing the endoplasmic reticulum folding capacity in *A. thaliana*.

Figure 4:
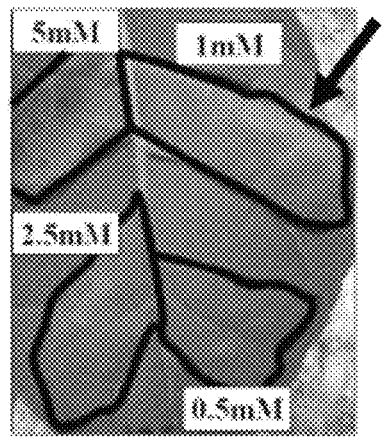
FIG. 4A shows that 4-PBA is not toxic to plant cells.
FIG. 4B shows that 4-PBA is capable of inducing BiP gene expression in a tobacco plant.
Figure 4:
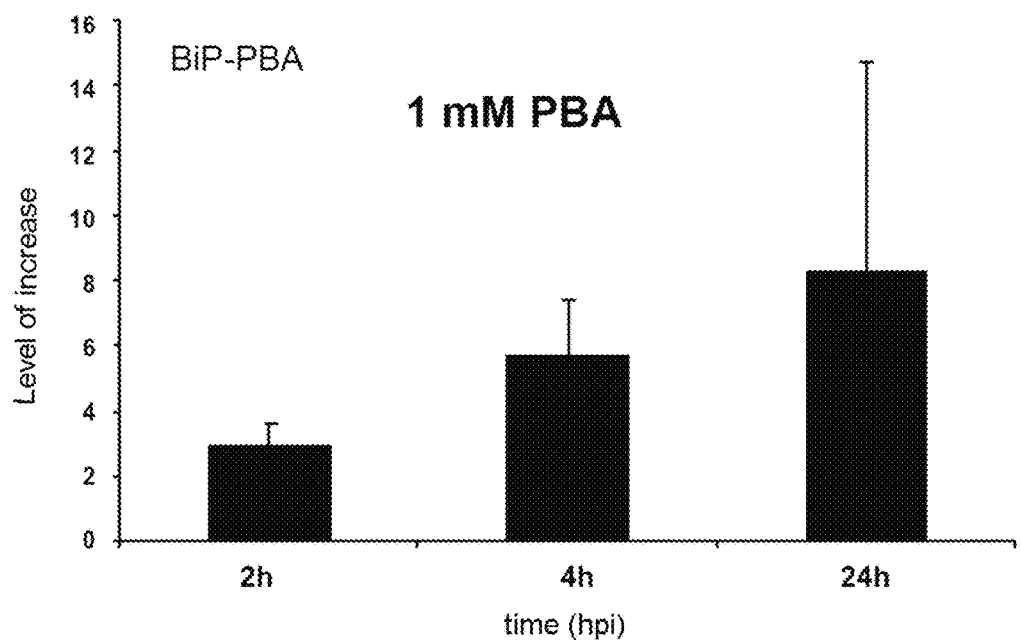
Figure 5:
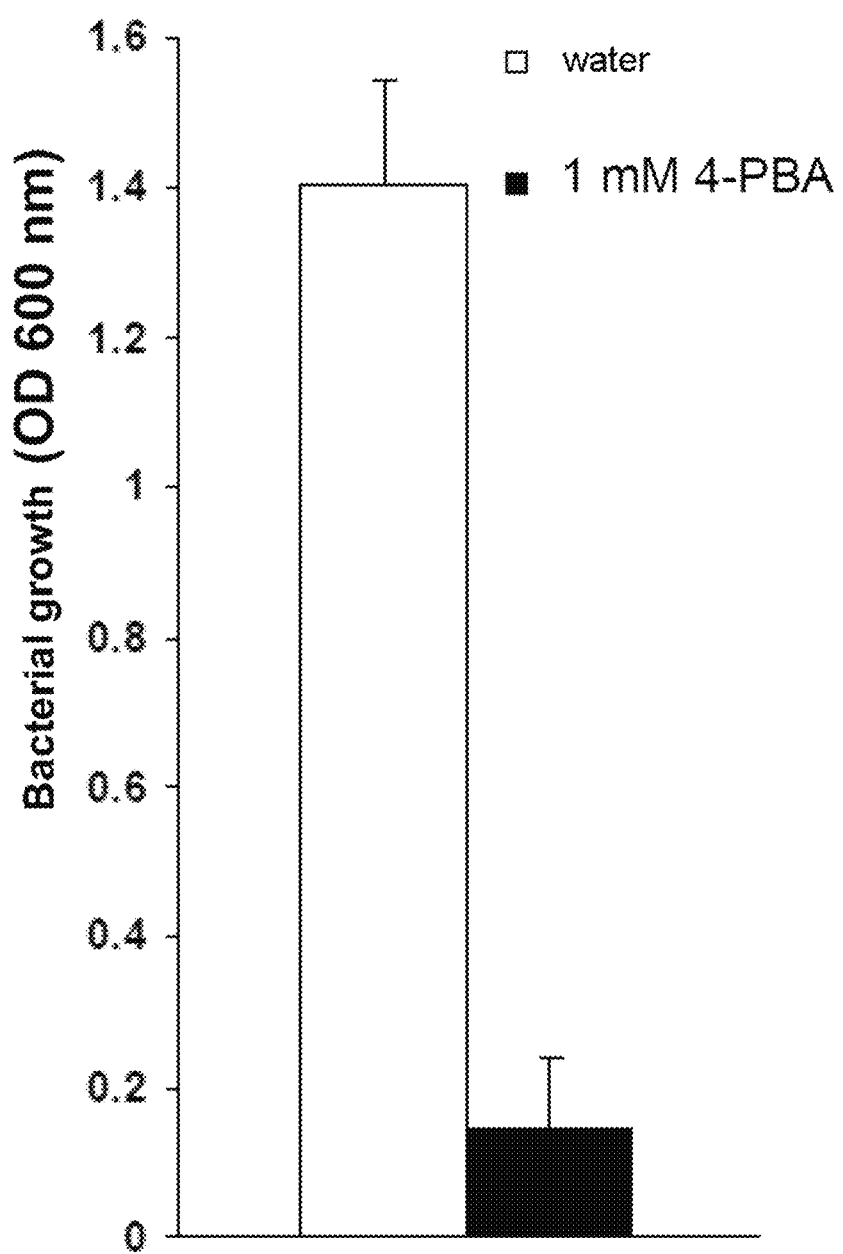
FIG. 5 shows that 4-PBA is capable of inhibiting bacterial growth.

The results obtained for tobacco are presented in FIG. 4. They demonstrate that 4-PBA at the concentrations used to inhibit hypersensitive cell death in the plants (FIGS. 1 and 2) or bacterial growth (FIG. 5) is not toxic to the plant cells (FIG. 4A, arrow). Moreover, these results clearly show that 4-PBA, as is the case in thale cress, is capable of inducing BiP gene expression in tobacco (FIG. 4B), which once again suggests that 4-PBA appears to act on the endoplasmic reticulum folding capacity in order to repress hypersensitive cell death induced by cryptogein in tobacco (data not shown).

Example 3

Antibacterial Properties of 4-PBA

Materials and Methods

The effect of 4-PBA on phytopathogenic bacteria was tested in vitro on the bacterial strain Xcm race 20. The strain was cultured in King B liquid medium in the presence or absence of 4-PBA. The 4-PBA solution was prepared extemporaneously as described above. The nutritive medium was inoculated either using glycerol stocks, or using bacterial colonies freshly cultured in solid medium. The nutritive medium was then supplemented with the 4-PBA solution in order to achieve a final concentration of 1 mM (final volume of 10 ml). The controls were supplemented with a comparable volume of water. The tubes were then incubated overnight (approximately 16 hours) with gentle shaking at 30° C. The bacterial growth was then measured by nephelometry by measuring the absorbance of an aliquot of the bacterial cultures at 600 nm. This experiment was repeated three times. Each experiment contained one technical triplicate per condition, i.e. condition with 4-PBA and condition without 4-PBA. All the experiments gave comparable results. Similar data were obtained for the Xcm race 18 strain (data not shown).
Results The results obtained are presented in FIG. 5. They clearly show that the presence of 4-PBA in the culture medium strongly inhibits the growth of the *X. campestris* pv. *malvacearum* bacteria (race 20). These data suggest that 4-PBA has at least bacteriostatic properties, or even bactericidal properties.

The invention claimed is:

1. A method of destroying a phytopathogen and/or of inhibiting the growth of a phytopathogen for preventing or treating a plant disease caused by said phytopathogen, comprising a step of applying, to the plant or to the soil surrounding the plant, an efficient amount of 4-phenylbutyric acid, or one of the salts thereof, wherein the phytopathogen is chosen from bacteria, viruses and nematodes.

2. The method according to claim 1, wherein the 4-phenylbutyric acid, or one of the salts thereof, is applied pre-emergence of the plant.

3. The method according to claim 1, wherein the 4-phenylbutyric acid, or one of the salts thereof, is applied post-emergence of the plant.

4. The method according to claim 1, wherein the 4-phenylbutyric acid, or one of the salts thereof, is applied to the aerial parts of the plant, to the roots of the plant, to the seeds, tubers or bulbs of the plant, and/or to the fruits or grains of the plant.

5. The method according to claim 1, wherein the plant belongs to the family Malvaceae, to the family Solanaceae, to the family Rubiaceae, to the family Poaceae or Gramineae or to the family Vitaceae.

* * * * *